US011033409B2

(12) United States Patent
Kalmar et al.

(10) Patent No.: US 11,033,409 B2
(45) Date of Patent: Jun. 15, 2021

(54) PROSTHESIS DEVICE

(71) Applicant: OTTO BOCK HEALTHCARE PRODUCTS GMBH, Vienna (AT)

(72) Inventors: Janos Kalmar, Vienna (AT); Roland Pawlik, Vienna (AT); Florian Fuchs, Hollabrunn (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 0 days.

(21) Appl. No.: 15/761,578

(22) PCT Filed: Sep. 20, 2016

(86) PCT No.: PCT/EP2016/072331
§ 371 (c)(1),
(2) Date: Mar. 20, 2018

(87) PCT Pub. No.: WO2017/050779
PCT Pub. Date: Mar. 30, 2017

(65) Prior Publication Data
US 2018/0338843 A1    Nov. 29, 2018

(30) Foreign Application Priority Data
Sep. 24, 2015   (DE) .......................... 102015116133.8

(51) Int. Cl.
*A61F 2/54* (2006.01)
*A61F 2/78* (2006.01)
*A61F 2/70* (2006.01)
*A61F 2/58* (2006.01)
*A61F 2/68* (2006.01)
(Continued)

(52) U.S. Cl.
CPC ................ *A61F 2/70* (2013.01); *A61F 2/588* (2013.01); *A61F 2/78* (2013.01); *A61F 2002/5016* (2013.01); *A61F 2002/5072* (2013.01); *A61F 2002/6836* (2013.01); *A61F 2002/6845* (2013.01); *A61F 2002/701* (2013.01);
(Continued)

(58) Field of Classification Search
CPC ...... A61F 2002/7862; A61F 2002/6872; A61F 2002/7635
USPC .......................................................... 623/58
See application file for complete search history.

(56) References Cited

U.S. PATENT DOCUMENTS

| 4,084,267 A | 4/1978 | Zadina |
| 4,114,464 A | 9/1978 | Schubert et al. |

(Continued)

FOREIGN PATENT DOCUMENTS

| CN | 101675903 A | 3/2010 |
| CN | 102258403 A | 11/2011 |

(Continued)

OTHER PUBLICATIONS

U.S. Appl. No. 62/279,733, filed Jan. 16, 2016.*
PCT International Search Report for PCT International Patent Application No. PCT/EP2016/072331, dated Dec. 7, 2016.

*Primary Examiner* — David H Willse
(74) *Attorney, Agent, or Firm* — Holland & Hart LLP

(57) ABSTRACT

A prosthesis device having a tension element fastened to a tensile force brace, which drives a movable component of a prosthesis device upon applying a tension force, wherein a sensor device is allocated to the tension element which detects the actuation of the tension element and activates a motor allocated to the movable component.

22 Claims, 2 Drawing Sheets

(51) Int. Cl.
  *A61F 2/76* (2006.01)
  *A61F 2/50* (2006.01)
(52) U.S. Cl.
  CPC ............... *A61F 2002/7635* (2013.01); *A61F 2002/7862* (2013.01)

(56) References Cited

U.S. PATENT DOCUMENTS

| | | |
|---|---|---|
| 4,258,411 A | 3/1981 | Bell |
| 4,258,441 A | 3/1981 | Bell |
| 4,604,098 A | 8/1986 | Seamone et al. |
| 5,413,611 A | 5/1995 | Haslam, II et al. |
| 8,021,428 B2 | 9/2011 | Bartish, Jr. et al. |
| 8,480,759 B2 * | 7/2013 | Pacanowsky ......... A61F 2/7812 623/36 |
| 9,861,500 B2 | 1/2018 | Puchhammer |
| 2007/0250179 A1 | 10/2007 | Latour |
| 2010/0069798 A1 | 3/2010 | Cheng et al. |
| 2014/0228973 A1 * | 8/2014 | Porter ...................... A61F 2/78 623/33 |
| 2017/0203432 A1 * | 7/2017 | Andrianesis .............. A61F 2/54 |

FOREIGN PATENT DOCUMENTS

| | | | |
|---|---|---|---|
| CN | 103284822 A | 9/2013 | |
| DE | 821690 C | 11/1951 | |
| DE | 2639143 A1 | 3/1977 | |
| DE | 2607499 A1 | 9/1977 | |
| DE | 27 06 408 A1 * | 8/1978 | ............. A61H 3/008 |
| DE | 102007035965 A1 | 2/2009 | |
| FR | 2851156 B1 | 8/2004 | |
| RU | 1806789 A1 * | 4/1993 | ............... A61F 2/56 |
| RU | 1806789 A1 | 4/1993 | |
| RU | 2063194 C1 | 7/1996 | |
| SU | 429810 A1 | 5/1974 | |
| SU | 1627172 A1 * | 2/1991 | ............... A61F 2/56 |

\* cited by examiner

PROSTHESIS DEVICE

TECHNICAL FIELD

The invention relates to a prosthesis device with a tensioning element which is fastened to a body harness and which drives a movable component of the prosthesis device when a tensile force is applied. The prosthesis device is configured in particular as a prosthetic arm.

BACKGROUND

Prostheses replace missing or lost limbs. In addition to purely cosmetic prostheses which simply replace the form of the missing limb, most modern prostheses attempt to replace one or more functions of the limb or to provide a functionality similar to that of a natural limb.

Lower-limb prostheses can be configured as prosthetic feet, which are fastened to a lower leg socket. More complex prostheses replace a knee joint, including single-axis blocking knee joints, multi-link knee joints, computer-controlled passive knee joints and driven knee joints of varying degrees of complexity. There are additionally prosthesis devices for patients with exarticulation of the hip.

The natural upper extremities are able to perform a large number of movements. The gripping and holding function of the hand, various rotation movements of the forearm and the high degree of mobility in the shoulder joint permit a large number of actions and movements, which can be simulated only with difficulty in an artificial system. In the case of prosthesis devices of the upper extremity, there are also different degrees of complexity ranging from simple hooks and grippers to driven prosthetic hands or motor-driven, myoelectric-controlled prosthetic arms.

Alongside highly complex, computer-controlled, sensor-based prosthesis devices, there is still a need for comparatively simple mechanical prosthesis devices which are actuated by what are called body harnesses. In these cases, a movable component of a prosthesis of the upper extremity is actuated by a shoulder movement, for example a movement of the shoulder of the contralateral and intact limb. A movable component can be moved in a direction either against the force of gravity or against an opposing force, e.g. a spring force. If active functions of a prosthesis device are triggered exclusively via a force by means of a body harness, such prostheses are referred to as body-powered prostheses. Compared to prostheses with electric drives, body-powered prostheses are directly controllable and have proprioceptive feedback.

A common application of body-powered prostheses is one in which a gripper or gripping element is opened counter to an opposing force, in particular a spring force, via the body harness. The opposing force can be applied via compression springs, tension springs or rubber rings, or pneumatically, or in some other way, and thus generates the gripping force. Since a high gripping force is advantageous in many activities, comparatively strong springs or rubber rings or force-generating elements are fitted. This opposing force has to be overcome when opening the gripper, i.e. applied by the patient by means of the body harness. Permanently working against the comparatively high opposing forces can lead to early fatigue or health problems for the patient.

DE 26 39 143 C2 relates to a gear for an orthosis or prosthesis, for converting a rotation movement of a drive unit into a reciprocating motion of a moved part of an orthosis or prosthesis. The gear has a rotatably mounted structural part, which is coupled to the drive unit and has a thread, and, engaging with the structural part, a gear part guided non-rotatably on the housing. The structural part consists of a hollow cylinder open at one end, with an inner thread and an outer thread with oppositely directed pitches. One end of a cable pull or chain pull is fixed to a screw spindle interacting with the inner thread, and the other end is fixed to a sleeve interacting with the outer thread. The gear is configured in the manner of a double spindle, the effect of which is that the tensile forces acting on the cable pull or chain pull are substantially constant over the entire displacement path.

DE 821 690 B relates to a prosthetic hand with a hollow hand body in which a cam disk is arranged. By way of rods and tensioning brackets, a rotation of the cam disk is converted into a movement of the fingers in order to open or close the hand.

DE 26 07 499 C3 relates to a drive device for the fingers of an artificial hand, in which a movable thumb and at least one finger moved in an opposite direction to the thumb are driven by motor with the aid of a self-locking gear. A worm is in direct engagement with toothed wheels secured to the movable fingers and to the thumb. The toothed wheels mesh with the worm at diametrically opposite sides, wherein the worm is driven with the aid of a reversible gear.

U.S. Pat. No. 4,604,098 A relates to a prosthetic arm having a forearm part, an elbow joint with locking elements and engaging elements to prevent bending of the elbow, and an upper arm part connected to the forearm part via the elbow joint. The forearm part is moved relative to the upper arm part about the elbow joint via a motor. The locking means can be disengaged via an unlocking mechanism in order to permit bending. The bending movement and the locking or unlocking are controlled electronically.

SUMMARY

The object of the present invention is therefore to make available a prosthesis device which ensures fatigue-free work and places less strain on the patient.

According to the invention, this object is achieved by a prosthesis device having the features of the main claim. Advantageous embodiments and developments of the invention are disclosed in the subclaims, the description and the figures.

In the prosthesis device according to the invention, with a tensioning element which is fastened to a body harness and which drives a movable component of the prosthesis device when a tensile force is applied, provision is made that the tensioning element is assigned a sensor device which detects the actuation of the tensioning element and activates a motor assigned to the movable component. The sensor device detects whether and how tensile forces are applied to the tensioning element via the body harness. The sensor device measures the extent of the applied tensile force. The sensor device forwards the correspondingly generated sensor signals to a control device, which is coupled to the sensor device. A motor is activated via this control device, i.e. started up according to the sensor signals, in order to drive the movable component or at least to support the intended movement of the movable component. Direct feedback to the user of the prosthesis device is provided via the body harness, such that the advantages of a conventional body-powered prosthesis are retained. At the same time, the force to be applied by the body harness is reduced, since only a reduced force has to be applied in order to actuate the movable component counter to the force of gravity or counter to the spring force, because the motor supports the intended movement. In contrast to prostheses that are operated exclusively by external force, it is advantageous if an actuating force is still applied to the movable component via the body harness. Similarly to servo-assisted steering, the intended movement is effected via the tensioning element; only the force to be applied by the patient is reduced.

The movable component can preferably be configured as a mechanical gripping element or gripper or as a joint component. The mechanical gripper is preferably opened counter to an opposing force, in particular a spring force, and, when the tensile force and the motor support cease, the mechanical gripper closes, such that no further force then has to be applied for secure gripping or fixing of an object. The holding force is exerted by the pretensioning or the force-applying element. In principle, it is also possible and provided for that the closure movement of the gripper is performed by the body harness and the tensioning element, according to the invention with the support of a motor. When the tensile force and the motor support cease, the gripper is then opened as a result of a spring force, in an opposite embodiment opened counter to a spring force. Alternatively or in addition to a purely mechanical gripper, provision is made that a joint component of the prosthesis device is also driven in such a manner. A movement of the prosthesis component in a defined direction, whether counter to a spring force or counter to the force of gravity, is provided. For example, prosthesis components can be moved about a pivot axis counter to spring forces, wherein the spring forces keep the prosthesis component in a starting position. Depending on the direction of force, the prosthesis component can then be pivoted or rotated in one or other direction. The mechanical gripper can have two or more hook-shaped gripping elements and can in particular be configured itself as a hook. In addition to a gripper with two fingers, it is also possible to provide a prosthetic hand as gripper.

In a development of the invention, provision is made that the support force applied by the motor is proportional to the tensile force applied by the tensioning element. This ensures direct proprioceptive feedback; the more force is applied via the body harness, the greater the tensile force applied to the movable component and the greater the support force additionally applied via the motor. The stated advantages of the direct feedback are seen in particular in the closure of the mechanical gripper by the tensile force and the motor support. The pressure point and the grip point are likewise adjustable.

The motor is preferably coupled to the tensioning element and/or to the movable component via a gear. The interposition of one or more gears makes it possible to use small, fast and light motors, which is particularly advantageous as regards the preferred use in upper-limb prostheses, since there is little space available in these for fitting motors and energy accumulators. As gears, it is possible to use cable winding gears, toothed belt gears, toothed wheel gears, drum gears, friction gears or planetary gears. In particular, cable winding gears are advantageously used since, in conventional mechanical grippers, the force transmission takes place from the contralateral shoulder to the mechanical gripper via a cable pull, if appropriate with deflection rollers.

The geared transmission and also the proportionality factor are advantageously adjustable in order to permit adaptation to different types of use. It is likewise advantageous if the proportionality factor of the support force by the motor is adjustable, likewise the force amplification or the support performance by the motor. Thus, if support is not required, the motor can be supplied with less energy or uncoupled, as a result of which the duration of use of the prosthesis device is longer, since only as much support energy as is needed is supplied.

In a development of the invention, provision is made that the movable component is loaded with a spring force which counteracts the tensioning element and/or the motor. It is thereby possible to influence the opening or closing of the gripper, or the flexion or extension of the joint component, and, particularly in the case of a gripper, to permit a defined holding force without additional movement or additional input of energy. In the case of joint devices, the components can thereby be placed in relation to each other in a preferred setup, which can be changed only by applying a force starting from a defined threshold value.

The sensor device can have a force sensor in the tensioning element or in a deflection roller, in order to be able to provide a suitable additional force which, for example, is proportional to the force applied by the user. The proportionality factor does not have to be linear across the force; the additional force via the motor can be raised more than proportionally as the force increases. It is also possible that the maximum applied force is limited, i.e. that the sum of the force transmitted to the movable component via the tensioning element is limited to a maximum value.

In one embodiment of the invention, the sensor device or the force sensor is configured as a force-measuring bolt. The sensor is preferably configured as a force-measuring bolt inside the tensioning element, such that simple determination of the force acting inside the tensioning element is permitted. The force can be measured via a signal amplifier, and the force additionally to be supplied by the motor can be applied proportionally to the tensile force. In addition to a linear proportionality, it is also possible to provide progressive or degressive proportionalities in order, for example, to provide very considerable support when particularly high forces are applied by the tensile force.

Alternatively or in addition to a direct arrangement of the sensor inside the tensioning element, a force-measuring device can also be arranged in a deflection roller or on a gear element, in order there to detect the tensile force applied via the tensioning element or the body harness and to activate the motor.

The motor can be assigned to the tensioning element and/or to the movable component via a coupling, such that, if the motor fails or the energy accumulator becomes depleted, the movable component can still be actuated as usual by the tensioning element. The motor can thus be switched on between the tensioning element and the movable component or if appropriate uncoupled therefrom. The coupling can be embodied, for example, as a centrifugal coupling or a spring-loaded release coupling.

By way of a coupling, it is also possible for the prosthesis device to have a modular construction, that is to say a conventional body-powered prosthesis with an additional component in the form of the motor with the control device can be offered as an accessory component in order to permit an additional and improved functionality of the prosthesis device.

The movable component, in particular the movable gripper, is fastened exchangeably on the prosthesis device, in order to be able to provide different functionalities for different actions.

The tensioning element can be configured as a cable pull or strap which is actuated via the body harness. The tensioning cable or tensioning element can be guided in a cable sheath or sleeve, wherein the endpiece is free and is fastened via a deflection roller, and if appropriate a support roller, on the movable component, in particular the mechanical gripper.

The tensioning element can be routed at least partially inside a prosthesis socket, wherein the tensioning element is adapted to the respective patient or user by an orthopedist. Both the length of the tensioning element and also the gear ratios and amplifications are adapted individually to the respective patient and are adjustable.

The motor can act on the tensioning element and thereby increase the tensile force applied to the movable component via the tensioning element, i.e. use the tensioning element as the only element for transmitting force to the movable component. Alternatively, the motor can be coupled to the movable component, separately from the tensioning element, and can be coupled directly to the movable component for example via a toothed wheel gear or a friction gear, if appropriate with an interconnected freewheel. The force transmission from the motor to the movable component does not then take place via the tensioning element, but separately, as a result of which no changes have to be made to the structure of the original prosthesis device. Only the sensor device has to be assigned to the tensioning element, and the support device with motor, and if appropriate with gear and controller, has to be coupled mechanically to the movable component in a force-transmitting manner.

BRIEF DESCRIPTION OF THE DRAWINGS

Illustrative embodiments of the invention are set out below and are explained in more detail with reference to the attached figures, in which.

DETAILED DESCRIPTION

Figure 1:
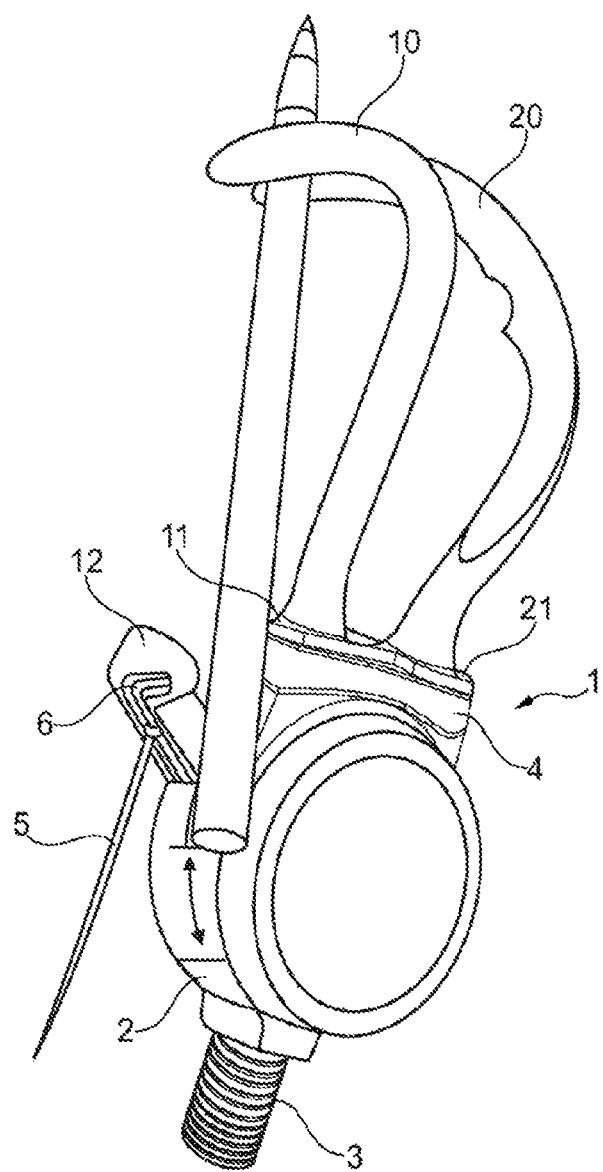
FIG. 1 shows a movable component in the form of a gripper.

A movable component 1 in the form of a mechanical gripper, configured as a hook, is shown on its own in FIG. 1. The mechanical gripper 1 has a main body 2, at one end of which a fastening device 3 in the form of a thread is arranged or formed for the purpose of fixing to a prosthesis socket (not shown). Two fingers 10, 20, shaped like hooks and configured to grip objects (in the form of a pen in FIG. 1), are formed at the end of the main body 2 opposite the fastening device 3. A first finger 20 is fastened rigidly to the main body 2, and the second finger 10 is mounted pivotably on the main body 2, wherein the pivot axis (not shown) is configured in such a way that the second finger 10 can be moved away from the first finger 20, such that a space between the two fingers 10, 20 can be made larger or smaller. The movement of the second finger 10 away from the first finger 20 takes place counter to an opposing force which allows the two fingers 10, 20 to bear on each other in the non-actuated state. The opposing force is exerted via a rubber ring 4 which is placed around a base 11, 21, respectively, for the second finger 10 and first finger 20. The rubber ring 4 is placed in grooves and is thus mounted exchangeably on the two bases 11, 21. Depending on the intended use, and on the required holding force that is to be exerted between the two fingers 10, 20, different rubber rings 4 can be placed in the groove. If only a low holding force is required, a resilient rubber ring 4 is inserted; if a high holding force is required, a more stable rubber ring 4 is used that has less extensibility and elasticity and therefore greater resistance to an excursion.

The fingers 10, 20 can be fastened to the respective base 11, 21 in an exchangeable manner, for example screwed in, or inserted in some other way and fixed with form-fit engagement.

To move the second finger 10 away from the first finger 20, a tensioning element 5 is fastened to a third finger 12, which is coupled rigidly to the second finger 10. The tensioning element 5 is configured in the form of a tensioning strap or cable or a cable pull and is mounted with form-fit engagement on the third finger 12, in a groove 6 formed in the latter. The groove 6 extends along the proximal side of the third finger 12, i.e. the side directed toward the prosthesis socket, and permits a change of the leverage when force is transmitted from the tensioning element 5 to the second finger 10. The farther outward the tensioning element 5 is moved, the greater is the lever travel, as a result of which the force that has to be applied is reduced and at the same time the opening travel between the fingers 10, 20 is reduced. The third finger 12 is coupled to the second base 11 and protrudes from the latter, such that the second base 11 and therefore also the second finger 10 are pivoted about the pivot axis when a tensile force is applied by the tensioning element 5. The pivot axis is oriented substantially perpendicularly with respect to the substantially circular main surfaces of the disk-like main body 2. When the tensioning element 5 is pulled, the third finger 12, and with it also the second finger 10, moves downward in the direction of the arrows; when the tensile force is reduced, the third finger 12, and with it also the second finger 10, moves upward in the direction of the arrows, since the rubber ring 4 exerts the corresponding opposing force. The object to be gripped, a pen in the illustrative embodiment shown, is held between the first finger 20 and the second finger 10 and can be laid against the third finger 12.

In the case of a body-powered prosthesis, the actuation of the tensioning element 5 can take place exclusively via a movement of a part of the body, for example the shoulder of the treated or intact arm.

Figure 2:
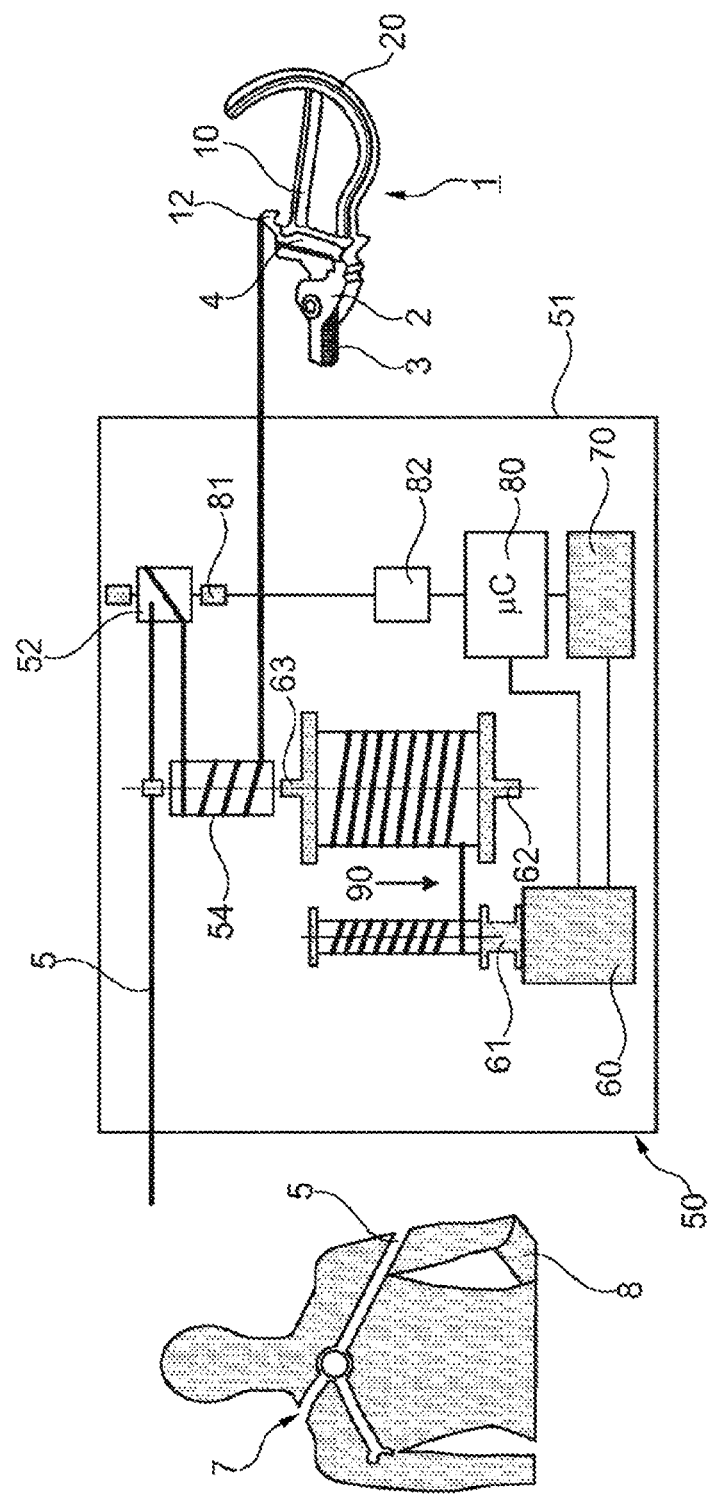
FIG. 2 shows a schematic illustration of the prosthesis device.

FIG. 2 shows the prosthesis device in a schematic illustration. A body harness 7, which is coupled to a prosthesis socket 8, is fitted on a patient, who is indicated on the left in the schematic illustration. The body harness 7 is fastened to the contralateral, intact shoulder and guided in the form of a loop around the shoulder. On the back, in the region of the upper thoracic vertebra, the loop is secured in a ring, to which a tensioning element 5 in the form of a tensioning strap is fastened. When the intact shoulder is moved forward, this has the effect that a tensile force is applied to the tensioning element 5. The tensioning element 5 is guided along the upper arm on the treated side, such that the tensioning element 5 is guided inside the prosthesis socket 8. In the embodiment shown, the tensioning element 5 is configured initially as a strap which, inside the prosthesis socket 8, is then coupled to a cable-shaped tensioning element 5, for example a wire pull, a cord, the core of a Bowden cable or the like, or transitions into a tensioning element 5 of such a kind.

A support device 50, shown schematically and on an enlarged scale, is arranged inside the prosthesis socket 8. The support device 50 can be constructed as a module and can have a housing 51 inside which the cable-shaped tensioning element 5 coming from the body harness 7 is guided. The tensioning element 5 is guided around a deflection roller 52, which is coupled to a sensor device in the form of a force-measuring bolt. From the deflection roller 52, the tensioning element 5 is guided by way of a support roller 54, and from there it is fastened to the third finger 12 of the movable component 1. FIG. 2 shows an alternative embodiment of the movable component in the form of a mechanical gripper 1 in which the main body 2 is not shaped as a circular disk and in which the element 4 generating the opposing force is not configured as a rubber ring but instead configured with a triangular contour and as a tension spring. When the tensioning element 5 is subjected by the body harness 7 to a tensile force in the direction away from the mechanical gripper 1, the deflection roller 52 is rotated, likewise the support roller 54, and the two fingers 10, 20 are thereby moved away from each other.

An electric motor 60 with a drive shaft 61 is arranged inside the support device 50. The motor 60 is supplied with energy via an electrical energy accumulator 70. The motor 60 is assigned a control device 80, by which the motor 60 is activated or deactivated. In the illustrative embodiment shown, the deflection roller 52 is assigned a sensor device 81 in the form of a force-measuring bolt. When a tensile force is applied to the tensioning element 5, the deflection roller 52 is subjected to a torque and to a force which is measured via the sensor device 81. The signal is sent to the control device 80 via a signal amplifier 82. When a tensile force within the tensioning element 5 is detected at the deflection roller 52, the motor 60 is activated via the control device 80. The drive shaft 61 is driven. An output shaft 62 is coupled to the drive shaft 61 via a cable winding gear 90. The drive shaft 61 winds up a coupling cable and thereby rotates the output shaft 62, which is coupled to the support roller 54 via a coupling 63. The coupling 63 can be configured as a centrifugal coupling or spring-loaded toothed-wheel coupling. It is likewise possible that the coupling has a serrated spur toothing which is oriented such that force is transmitted only in the direction of support of the tensile force of the tensioning element 5.

In the illustrative embodiment shown, the support roller has to rotate to the left in order to open the mechanical gripper 1; the flanks of the serrated spur toothing would then fall away to the right. Instead of a cable winding gear as shown, it is possible for toothed wheel gears, toothed belt gears, drum gears or friction gears or planetary gears to be formed between the motor 60 and the support roller 54. By means of the different diameters of the drive shaft 61 and of the output shaft 62, it is possible to achieve different transmission ratios of the cable winding gear 90, and adaptation can easily be achieved by exchanging the respective shafts or the drums on the respective shafts 61, 62 and/or the support roller 54.

The support force applied by the motor 60 can be adjusted via the control unit 80. The adjustment can be made according to the planned use of the mechanical gripper 1 or according to the personal preference of the user.

Instead of a force-measuring bolt as the sensor device 81 on the deflection roller 52, it is also possible and provided for that the sensor device 81 is arranged along the course of the tensioning cable 5, for example in the form of a tensile force sensor, which determines the tensile force effective in the tensioning element 5. The sensor data can be transmitted to the signal amplifier 82 wirelessly or also by wire. Along most of its length, the tensioning element 5 can be routed through a sheath in order to avoid chafing of the tensioning element 5 on the skin or on the clothes of the user.

The support device 50 can be configured as a module and simply fitted onto an existing body-powered prosthesis. The tensioning element 5 simply has to be placed around the deflection roller 52 and the support roller 54, which means only a slight lengthening of the tensioning element 5 compared to direct fastening on the mechanical gripper 1. Should the energy accumulator 70 be empty or the motor 60 have a defect, the prosthesis device can continue to be used without any great limitation in respect of its function; only the comfort is reduced.

Instead of force being applied by the motor 60 via the tensioning element 5, in an alternative embodiment the drive is coupled directly to the movable second finger 10. The support device 50 can be integrated in the main body 2 and coupled in a force-transmitting manner to the movable finger 10 via a gear arrangement, for example a friction gear or a toothed wheel gear with a suitable coupling 63. If a tensile force is then detected by the sensor device 81, which can also be arranged directly in the tensioning element 5, the sensor device 81 can transmit this by cable or wirelessly to the signal amplifier 82 of the control device 80, whereupon the motor 60 is then activated. In this way, it is possible to dispense with loading of the tensioning element 5 by the additionally applied motor force. Modifications to the attachment of the tensioning element 5 to the mechanical gripper 1 are not necessary. The support device 50 is provided as a separate mechanical component, in the form of a prefabricated module with the motor 60 and the integrated controller 80 together with the energy accumulator 70, and simply has to be fastened in the main body 2 or on the main body 2. The force of the motor 60 is then transmitted via a suitable coupling 63 in order to drive the movable finger 10. The extent of the force which is to be applied, likewise the duration for which it is to be applied, are defined by the tensile forces that are determined in the sensor device 81. It is possible to adopt a linear proportionality between the tensile force applied via the tensioning element 5 and the additionally provided motor force; alternative proportionality factors are possible. A common aspect of both embodiments is that the functionality of the mechanical gripper 1 is maintained in the event of a failure of the support device 50.

The invention claimed is:

1. A prosthesis device, comprising:
    a body harness configured to be connected to a body part;
    a tensioning element which is fastened to the body harness and which drives a movable component of the prosthesis device when a tensile force is applied by the body part;
    a sensor device assigned to the tensioning element to detect the tensile force applied by the body part to the tensioning element and to activate a motor, the motor applying tension in the tensioning element to move or to assist movement of the movable component;
    wherein the body harness is configured to be connected to the body part on one side of a sagittal plane of the user's body, and the movable component is configured to be positioned on an opposite side of the sagittal plane of the user's body.

2. The prosthesis device as claimed in claim 1, wherein the movable component is configured as a mechanical gripper or joint component.

3. The prosthesis device as claimed in claim 1, wherein a support force applied by the motor is proportional to the tensile force applied by the tensioning element.

4. The prosthesis device as claimed in claim 1, wherein the motor is coupled to at least one of the tensioning element and the movable component via a gear.

5. The prosthesis device as claimed in claim 4, wherein the gear is configured as a cable winding gear, toothed belt gear, toothed wheel gear, drum gear, friction gear or planetary gear.

6. The prosthesis device as claimed in claim 4, wherein a geared transmission and a proportionality factor of the gear are adjustable.

7. The prosthesis device as claimed claim 1, wherein a support force provided by the motor is adjustable.

8. The prosthesis device as claimed in claim 1, wherein the movable component is loaded with a spring force which counteracts at least one of the tensioning element and the motor.

9. The prosthesis device as claimed in claim 1, wherein the sensor device has a force sensor in the tensioning element or in a deflection roller.

10. The prosthesis device as claimed in claim 9, wherein the force sensor is configured as a force-measuring bolt.

11. The prosthesis device as claimed in claim 1, wherein the motor is assigned to at least one of the tensioning element and the movable component via a coupling.

12. The prosthesis device as claimed in claim 1, wherein the motor drives the tensioning element or separately drives the movable component.

13. The prosthesis device as claimed in claim 1, wherein a first end portion of the tensioning element is fastened to the body harness and a second end portion of the tensioning element is fastened to the movable component, and the motor is operatively coupled to the tensioning element at a location between the first and second end portions.

14. A prosthesis device, comprising:
a body harness;
a movable component;
a motor operable to apply a support force to the movable component;
a tensioning element which is fastened to the body harness and which drives the movable component when a tensile force is applied;
a sensor device to detect actuation of the tensioning element and activate the motor, the motor applying tension in the tensioning element to move or to assist movement of the movable component;
at least one of a deflection roller, a support roller, and a coupling interposed between the tensioning element and the moveable component to engage and disengage the motor.

15. The prosthesis device as claimed in claim 14, wherein the movable component is configured as a mechanical gripper or joint component.

16. The prosthesis device as claimed in claim 14, wherein a support force applied by the motor is proportional to the tensile force applied by the tensioning element.

17. The prosthesis device as claimed in claim 14, further comprising a gear, the gear coupling the motor to at least one of the tensioning element and the movable component.

18. The prosthesis device as claimed in claim 17, wherein the gear is configured as a cable winding gear, toothed belt gear, toothed wheel gear, drum gear, friction gear or planetary gear.

19. The prosthesis device as claimed in claim 17, wherein the gear includes an adjustable geared transmission and an adjustable proportionality factor.

20. The prosthesis device as claimed claim 14, wherein the support force provided by the motor is adjustable.

21. The prosthesis device as claimed in claim 14, wherein the movable component is loaded with a spring force which counteracts at least one of the tensile force of the tensioning element and the support force of the motor.

22. A prosthesis device, comprising:
a body harness configured to be connected to a body part;
a tensioning element which is fastened to the body harness and which drives a movable component of the prosthesis device when a tensile force is applied by the body part;
a sensor device assigned to the tensioning element to detect the tensile force applied by the body part to the tensioning element and to activate a motor, the motor applying tension in the tensioning element to move or to assist movement of the movable component;
wherein the body harness is configured to be interposed in-line between the body part and the tensioning element, and the sensor device detects tension applied by the body part to the tensioning element via the body harness.

* * * * *